(12) United States Patent
Salman et al.

(10) Patent No.: US 9,636,003 B2
(45) Date of Patent: May 2, 2017

(54) MULTI-JET DISTRIBUTOR FOR AN ENDOSCOPE

(71) Applicant: EndoChoice, Inc., Alpharetta, GA (US)

(72) Inventors: Golan Salman, Atlit (IL); Amram Aizenfeld, Ramot Menashe (IL)

(73) Assignee: EndoChoice, Inc., Alpharetta, GA (US)

( * ) Notice: Subject to any disclaimer, the term of this patent is extended or adjusted under 35 U.S.C. 154(b) by 463 days.

(21) Appl. No.: 14/317,863

(22) Filed: Jun. 27, 2014

(65) Prior Publication Data

US 2015/0005581 A1    Jan. 1, 2015

Related U.S. Application Data

(60) Provisional application No. 61/840,706, filed on Jun. 28, 2013.

(51) Int. Cl.
*A61B 1/015* (2006.01)
*A61B 1/00* (2006.01)

(52) U.S. Cl.
CPC .......... *A61B 1/015* (2013.01); *A61B 1/00091* (2013.01); *A61B 1/00096* (2013.01); *A61B 1/00177* (2013.01); *A61B 1/00181* (2013.01)

(58) Field of Classification Search
CPC .. A61B 1/00091; A61B 1/015; A61B 1/00128
USPC ................... 600/118, 153–159, 169
See application file for complete search history.

(56) References Cited

U.S. PATENT DOCUMENTS

| | | | | |
|---|---|---|---|---|
| 5,630,798 A * | 5/1997 | Beiser ................ | A61B 1/00135 |
| | | | 604/30 |
| 5,685,821 A * | 11/1997 | Pike ................... | A61B 1/00039 |
| | | | 600/118 |
| 5,810,770 A * | 9/1998 | Chin ................... | A61M 3/0258 |
| | | | 604/65 |
| 6,095,971 A * | 8/2000 | Takahashi ............... | A61B 1/12 |
| | | | 600/118 |
| 7,918,788 B2 * | 4/2011 | Lin ....................... | A61B 1/123 |
| | | | 600/133 |
| 8,353,860 B2 * | 1/2013 | Boulais ............... | A61B 1/00085 |
| | | | 604/27 |
| 9,289,110 B2 * | 3/2016 | Woolford ........... | A61B 1/00039 |
| 2007/0100206 A1 * | 5/2007 | Lin ....................... | A61B 1/123 |
| | | | 600/156 |
| 2007/0118015 A1 * | 5/2007 | Wendlandt ......... | A61B 1/00156 |
| | | | 600/146 |

* cited by examiner

*Primary Examiner* — Matthew J Kasztejna
(74) *Attorney, Agent, or Firm* — Novel IP

(57) ABSTRACT

The present specification describes a jet distributor provided to supply fluids to each of a plurality of jet openings in a multi jet endoscope tip. In an embodiment, the jet distributor is supplied with a fluid from a jet pump. The jet distributor includes at least two fluid channels to provide the fluid supplied via the jet pump to the front-jet, right-side-jets and left-side-jets in the endoscope tip. The jet-distributor includes a motor which rotates a rotating plug. The rotating plug includes an internal fluid pathway which becomes intermittently aligned with each of a plurality of fluid output channels in the jet distributor as the plug rotates, thereby providing fluid in a successive manner to the jets in the endoscope tip.

13 Claims, 14 Drawing Sheets

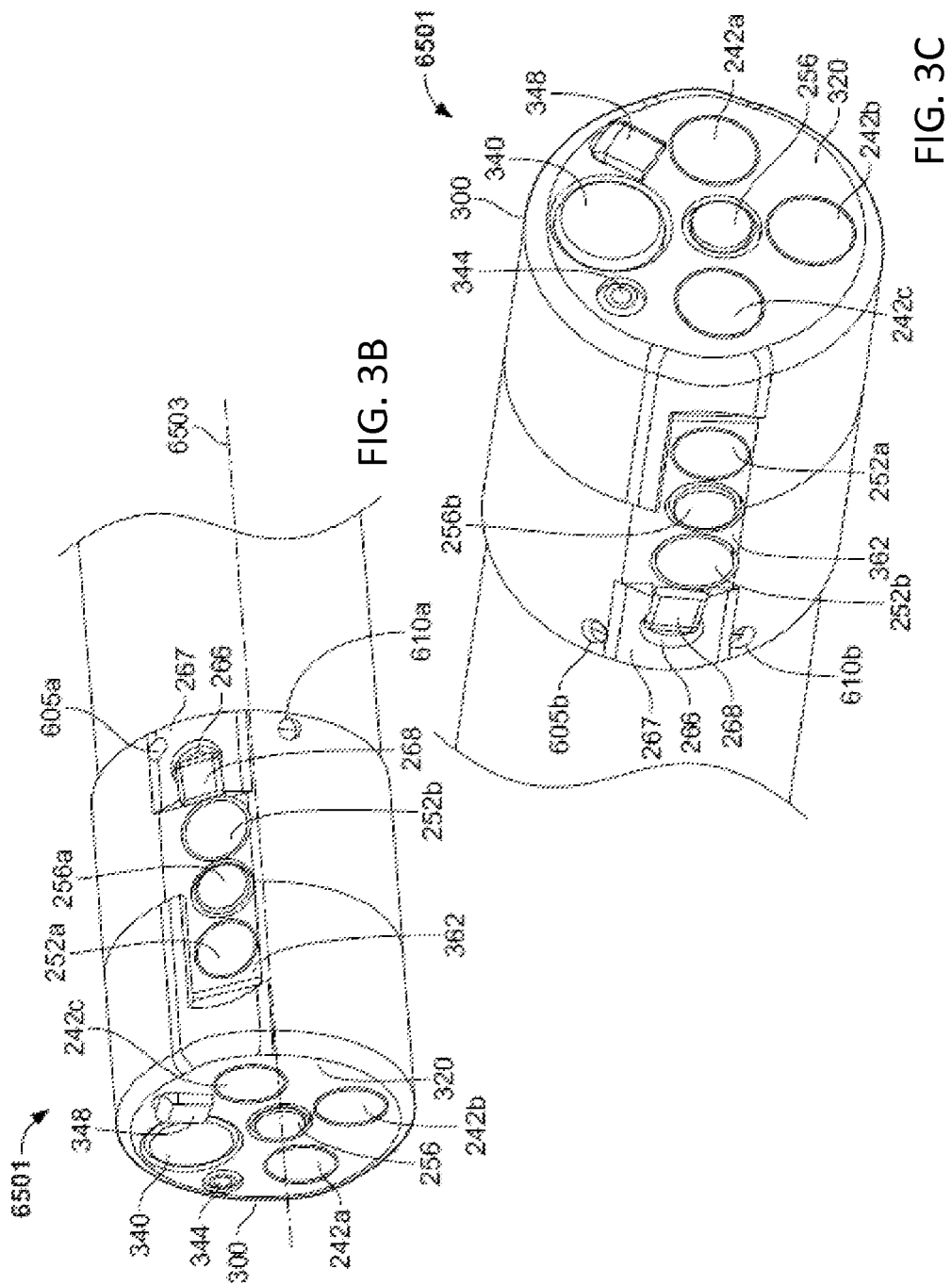

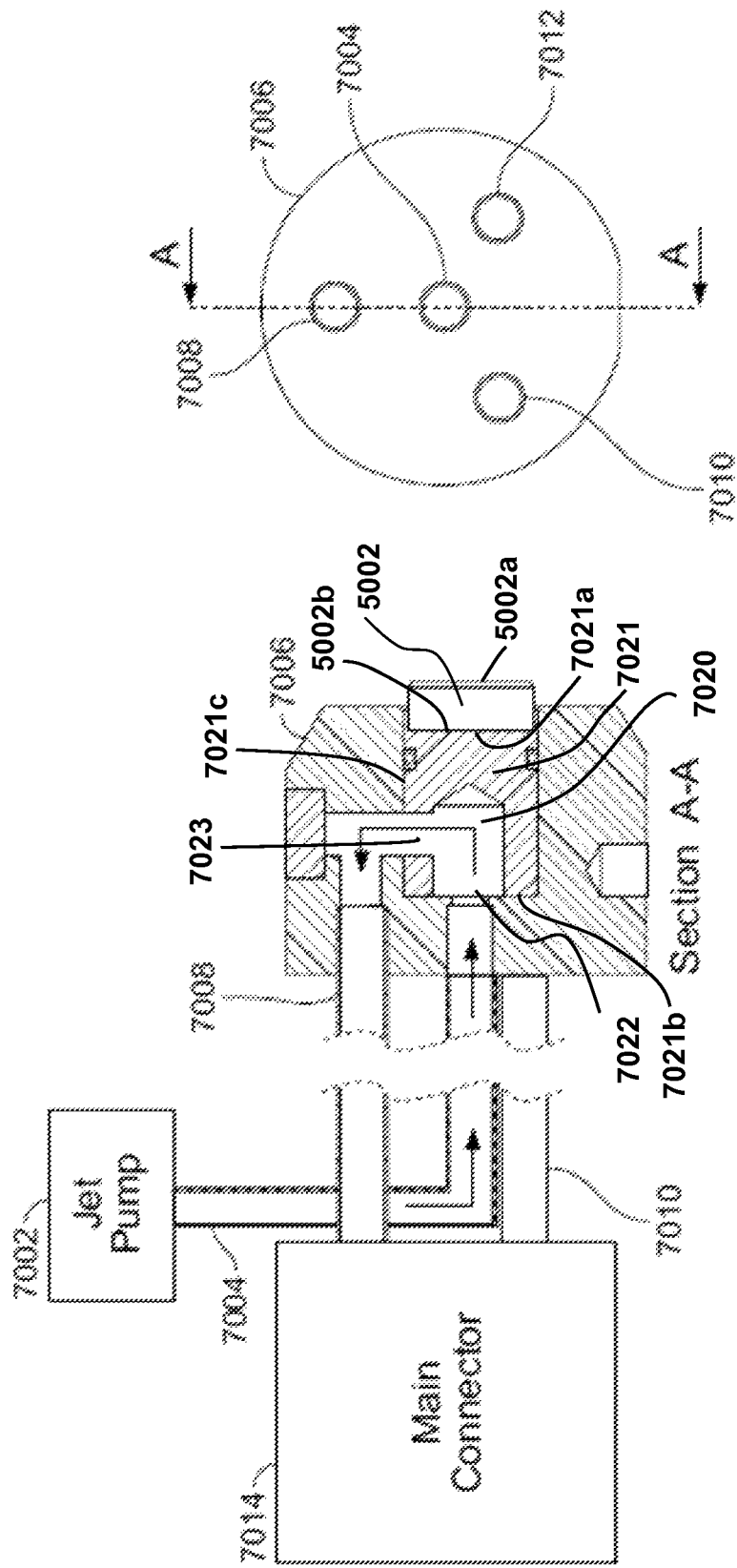

MULTI-JET DISTRIBUTOR FOR AN ENDOSCOPE

CROSS-REFERENCE TO RELATED APPLICATIONS

The present application relies on U.S. Provisional Patent Application No. 61/840,706, entitled "Multi-Jet Distributor For An Endoscope" and filed on Jun. 28, 2013, for priority.

The present application is related to U.S. patent application Ser. No. 14/278,293, entitled "Multiple Viewing Elements Endoscope Having Two Front Service Channels" and filed on May 15, 2014.

All of the above-mentioned applications are herein incorporated by reference in their entirety.

FIELD

The present specification generally relates to an endoscope assembly comprising a front jet and two side jets being supplied with fluid via fluid channels and a multi jet distributor.

BACKGROUND

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others. Endoscopes may be inserted into the body's natural orifices or through an incision in the skin.

An endoscope is usually an elongated tubular shaft, rigid or flexible, having a video camera or a fiber optic lens assembly at its distal end. The shaft is connected to a handle, which sometimes includes an ocular for direct viewing. Viewing is also usually possible via an external screen. Various surgical tools may be inserted through a working channel in the endoscope for performing different surgical procedures.

Endoscopes, such as colonoscopes, gastroscopes and the like, that are currently being used, typically have a front camera for viewing internal organs, such as the colon, an illuminator, a fluid injector for cleaning the camera lens, and a working channel for inserting surgical tools in order to, for example, remove polyps found in the colon. Often, endoscopes also have fluid ("jet") injectors for cleaning a body cavity, such as the colon, into which they are inserted.

There is a need in the art for endoscopes which enable the concurrent supply of fluids to multiple fluid injectors or jet openings in the endoscope tip in order to quickly and efficiently clean a body cavity or a portion of the endoscope.

SUMMARY

The following embodiments and aspects thereof are described and illustrated in conjunction with systems, tools and methods, which are meant to be exemplary and illustrative, not limiting in scope.

There is provided herein, according to some embodiments of the specification, a tip section of an endoscope, the tip section comprising: at least one front-viewing element and at least one front illuminator associated therewith; at least one side-viewing element and at least one side illuminator associated therewith; a front working channel configured for insertion of a medical tool; and a side service channel configured for insertion of a medical tool.

Optionally, the tip section further comprises at least one front fluid injector configured for cleaning at least one of the front-viewing elements and at least one of the front illuminator.

Optionally, the tip section further comprises at least one side fluid injector configured for cleaning at least one of the side-viewing elements and at least one of the side illuminator.

The tip section may further comprise a pathway fluid injector for inflating and/or cleaning a body cavity into which the endoscope is inserted.

The front and side fluid injectors may be connected to a same fluid supply channel.

The endoscope may be a colonoscope, a flexible endoscope, or a gastroscope.

Optionally, the endoscope assembly comprises two side jet channel openings on each of the opposing sides of the endoscope. The side jet channel openings may be positioned close to at least one side-viewing element.

The plurality of side jet channel openings may have an obtuse angle of exit.

The plurality of side jet channel openings, in combination with a fluid distributor and fluid source, may operate in accordance with at least one predefined fluid delivery sequence, such as a continuous fluid stream, a fluid stream pulsing at different flow rates, a fluid stream being expelled at different timings with respect to the different side jet openings, a fluid stream at different pressures or any other suitable method as would be evident to persons of ordinary skill in the art.

Each of the plurality of side jet channel openings may operate using a different fluid delivery sequence.

The present specification discloses an endoscope assembly comprising a multi-distributor jet for supplying fluid to a plurality of jet openings on a tip of the endoscope. The multi-distributor jet is enclosed in a distributor housing and comprises: a distributor motor; a motor shaft coupled with the distributor motor; and a distributor disc coupled with the motor shaft. The distributor disc comprises an entering fluid pipeline for supplying the multi-distributor jet with the fluid and at least one exiting fluid pipeline for providing the fluid supplied by the entering fluid pipeline to the plurality of jet openings on the endoscope tip.

Optionally, the distributor housing further comprises a locking element for latching the distributor disc within the distributor housing. Optionally, the distributor disc further comprises a distributor plug for connection with the motor shaft. Optionally, the distributor disc further comprises a groove on an outer periphery to connect a locking element for latching the distributor disc within the distributor housing.

A jet pump may supply fluid, from a fluid source, to the entering fluid pipeline. The multi jet distributor may be connected to the endoscope via a main connector, and can also be coupled with a main control unit or a fuse box of the endoscope assembly.

A distributing rate within the multi jet distributor may vary between 30 revolutions per minute (rpm) to 100 rpm, and more specifically between 50 to 65 rpm.

The multi jet distributor may comprise three exit pipelines wherein the pipelines exiting from the multi jet distributor carrying fluid enter the endoscope via a main connector and exit at the jet openings located at the endoscope tip.

The multi jet distributor may comprise two exit pipelines wherein the pipelines exiting from the multi jet distributor carrying fluid enter the endoscope via a main connector and exit at the jet openings located at the endoscope tip.

The present specification also discloses a system for distributing fluid from a source external to an endoscope into a plurality of fluid channels positioned within the endoscope, comprising: a pump; a fluid distributor device having a fluid input channel coupled to said pump, a distributor rotating plug and a plurality of fluid output channels, wherein said distributor rotating plug includes an internal fluid pathway, said internal fluid pathway being in fluid communication with said fluid input channel and capable of being positioned, via rotational movement of said distributor rotating plug, into a plurality of configurations wherein, when in each of said plurality of configurations, said internal fluid pathway is in fluid communication with one of said plurality of said fluid output channels and is not in fluid communication with any one of the remaining said plurality of fluid output channels; a motor shaft coupled to said distributor rotating plug; a motor coupled to said motor shaft, wherein, upon activating the motor, the motor causes the distributor rotating plug to rotate, thereby intermittently aligning said internal fluid pathway with each of said plurality of fluid output channels, allowing fluid to move from said fluid input channel, through the internal fluid pathway and successively into each of said plurality of fluid output channels; and at least one endoscope connector comprising said plurality of endoscope fluid channels, wherein said plurality of endoscope fluid channels are in fluid communication with the plurality of fluid output channels.

Optionally, the system further comprises a distributing element attached to said distributor rotating plug and rotatably movable within said fluid distributor device, wherein said distributing element comprises said internal fluid pathway.

Optionally, the system further comprises a housing, wherein said housing comprises said fluid distributor device, said motor and said motor shaft. The housing may further comprise a locking element for fixedly positioning the fluid distributor device within the housing. The fluid distributor device may further comprise a groove on an outer surface of said fluid distributor device for receiving the locking element.

The fluid distributor device may be substantially cylindrical.

Optionally, the fluid distributor device comprises a housing having an external surface wherein each of the plurality of fluid output channels extends outward from said external surface.

Optionally, the fluid distributor device comprises at least three fluid output channels wherein each of said at least three fluid output channels is separately and individually connected to at least three endoscope fluid channels.

The at least one endoscope connector may be positioned within said endoscope. Alternatively, the at least one endoscope connector may be positioned within a main control unit external to said endoscope. The system at least one endoscope connector may comprise a plurality of connectors for connecting said plurality of endoscope fluid channels with said plurality of fluid output channels. Alternatively, the at least one endoscope connector comprises a single connector for connecting said plurality of endoscope fluid channels with said plurality of fluid output channels.

The distributor rotating plug may have a distributor rate ranging between 30 revolutions per minute (rpm) and 100 rpm.

The present specification also discloses a fluid distributor system, comprising: a housing; a fluid distributor device positioned within said housing, wherein said fluid distributor device has a fluid input channel, a distributor rotating plug and a plurality of fluid output channels, wherein said distributor rotating plug includes an internal fluid pathway, said internal fluid pathway being in fluid communication with said fluid input channel and capable of being positioned, via rotational movement of said distributor rotating plug, into a plurality of configurations wherein, when in each of said plurality of configurations, said internal fluid pathway is in fluid communication with one of said plurality of said fluid output channels and is not in fluid communication with any one of the remaining said plurality of fluid output channels; a motor shaft coupled to said distributor rotating plug; and a motor coupled to said motor shaft, wherein, upon activating the motor, the motor causes the distributor rotating plug to rotate, thereby intermittently aligning said internal fluid pathway with each of said plurality of fluid output channels, allowing fluid to move from said fluid input channel, through the internal fluid pathway and successively into each of said plurality of fluid output channels.

Optionally, the fluid distributor system further comprises a distributing element attached to said distributor rotating plug and rotatably movable within said fluid distributor device, wherein said distributing element comprises said internal fluid pathway.

The housing further may comprise a locking element for fixedly positioning the fluid distributor device within the housing. The fluid distributor device may further comprise a groove on an outer surface of said fluid distributor device for receiving the locking element. The housing may comprise an external surface wherein each of the plurality of fluid output channels extends outward from said external surface.

Optionally, the fluid distributor device comprises at least three fluid output channels.

The distributor rotating plug may have a distributor rate ranging between 30 revolutions per minute (rpm) and 100 rpm.

The aforementioned and other embodiments of the present invention shall be described in greater depth in the drawings and detailed description provided below.

BRIEF DESCRIPTION OF THE DRAWINGS

These and other features and advantages of the present invention will be appreciated, as they become better understood by reference to the following detailed description when considered in connection with the accompanying drawings, wherein:

FIG. 3B illustrates a perspective first side view of the tip section of the multi jet endoscope assembly of FIG. 3A;

FIG. 3C illustrates a perspective second side view of the tip section of the multi jet endoscope assembly of FIG. 3A;

FIG. 7A illustrates a sectional view of a distributor disc of a multi jet distributor, in accordance with an embodiment of the present specification; and FIG. 7B illustrates another sectional view of a distributor disc of a multi jet distributor, in accordance with an embodiment of the present specification.

DETAILED DESCRIPTION

In an embodiment, a jet distributor is provided to supply fluids to each of a plurality of jet openings in a multi jet endoscope tip as illustrated in FIGS. 3A through 3D. In an embodiment, the jet distributor is supplied with a fluid from a jet pump. The jet-distributor comprises at least two fluid channels to provide the fluid supplied via the jet pump to the front-jet, right-side-jets and left-side-jets in the endoscope tip. In various embodiments, the jet distributors of the present specification are intended for operation with a multiple viewing elements endoscope similar to those described in U.S. patent application Ser. No. 14/278,293 and related applications, entitled "Multiple Viewing Elements Endoscope Having Two Front Service Channels" and filed on May 15, 2014, which is herein incorporated by reference in its entirety.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention. In the description and claims of the application, each of the words "comprise" "include" and "have", and forms thereof, are not necessarily limited to members in a list with which the words may be associated.

Figure 1:
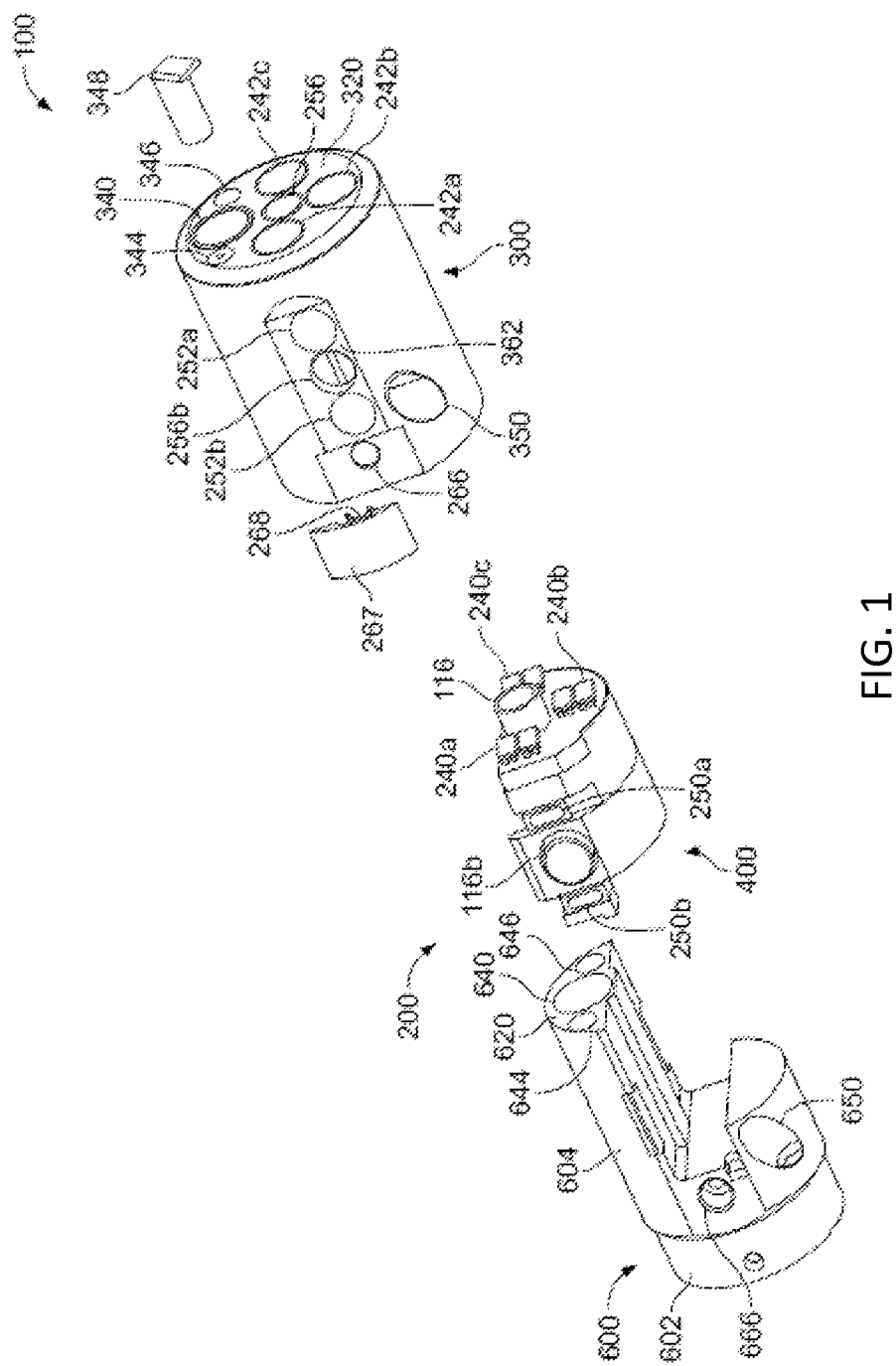
FIG. 1 illustrates an exploded view of a tip section of an endoscope assembly according to one embodiment of the present specification.

Reference is now made to FIG. 1, which shows an exploded view of a tip section 200 of a multi-viewing element endoscope assembly 100 comprising at least one front working/service channel, according to various embodiments. An aspect of some embodiments also relates to endoscope assembly 100 having the tip section 200 equipped with one or more side working/service channels.

It is noted that the term "endoscope" as mentioned to herein may refer particularly to a colonoscope or gastroscope, according to some embodiments, but is not limited only to colonoscopes and gastroscopes. The term "endoscope" may refer to any instrument used to examine the interior of a hollow organ or cavity of the body.

According to an embodiment, tip section 200 of endoscope 100 includes a tip cover 300, an electronic circuit board assembly 400 and a fluid channeling component 600.

According to some embodiments, fluid channeling component 600 may be configured as a separate component from electronic circuit board assembly 400. This configuration may be adapted to separate the fluid channels, at least one side service channel, such as side service channel 650, and at least one front working/service channel, such as working/service channel 640, which are located in fluid channeling component 600, from the sensitive electronic and optical parts which may be located in the area of electronic circuit board assembly 400. Thus, the component structure of the tip section 200 enables effective insulation of the plurality of electronic elements from the plurality of fluid channels.

Tip section 200 may be turnable by way of flexible shaft which is also referred to as a bending section, for example a vertebra mechanism.

In some embodiments, electronic circuit board assembly 400 is configured to carry a front viewing element 116 and at least one side viewing element 116b which may be similar to front viewing element 116 and may include a sensor such as but not limited to a Charge Coupled Device (CCD) or a Complementary Metal Oxide Semiconductor (CMOS) image sensor. In addition, electronic circuit board assembly 400 may be configured to carry a second side viewing element on the opposite side of side viewing element 116b, which may be similar to front viewing element 116 and may include a sensor such as but not limited to a Charge Coupled Device (CCD) or a Complementary Metal Oxide Semiconductor (CMOS) image sensor.

Electronic circuit board assembly 400 may further be configured to carry front illuminators 240a, 240b, 240c, which are, in one embodiment, associated with front viewing element 116 and are positioned to essentially illuminate the fields of view of front viewing element 116.

In addition, electronic circuit board assembly 400 may further be configured to carry side illuminators 250a and 250b, which are, in one embodiment, associated with side viewing element 116b and are positioned to essentially illuminate the fields of view of side viewing element 116b. Electronic circuit board assembly 400 may also be configured to carry side illuminators, which are associated with a second side viewing element that is positioned on the opposite side of side viewing element 116b, which may be similar to side illuminators 250a and 250b.

Front illuminators 240a, 240b, 240c and side illuminators 250a and 250b may optionally be discrete illuminators and may include a light-emitting diode (LED), which may be a white light LED, an infrared light LED, a near infrared light LED, an ultraviolet light LED or any other LED.

The term "discrete", concerning discrete illuminator, may refer to an illumination source, which generates light internally—in contrast to a non-discrete illuminator, which may be, for example, a fiber optic merely transmitting light generated remotely.

Figure 2A:
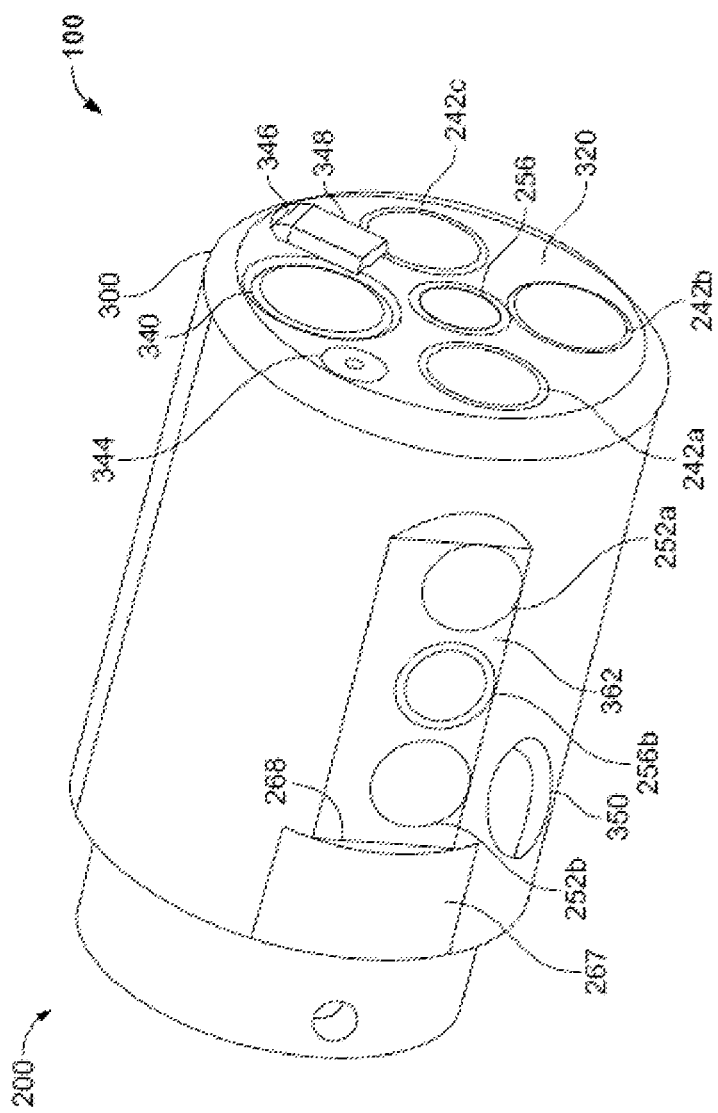
FIG. 2A illustrates a perspective view of a tip section of an endoscope assembly according to one embodiment of the present specification.
Figure 2B:
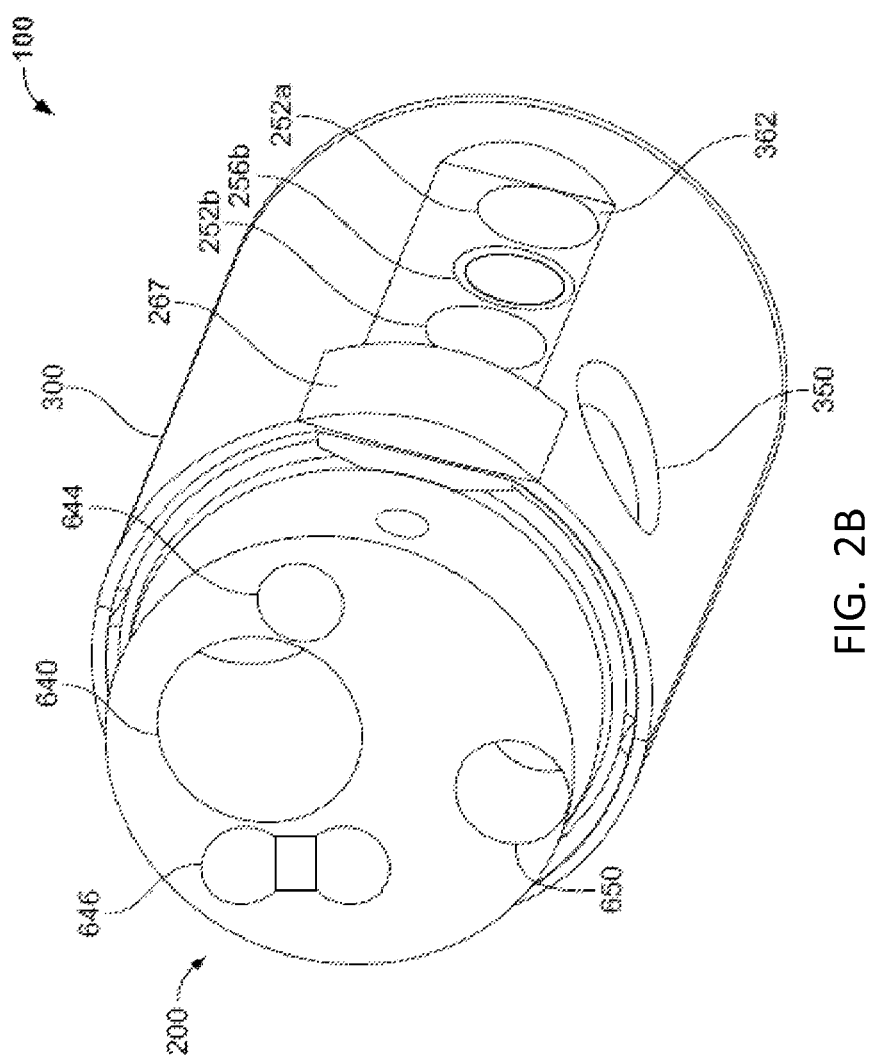
FIG. 2B illustrates another perspective view of a tip section of an endoscope assembly according to one embodiment of the present specification.

Reference is now made to FIG. 1 along with FIG. 2A and FIG. 2B, which show a perspective view of a tip section 200 of an endoscope assembly 100 according to an embodiment.

Tip cover 300 may be configured to fit over the inner parts of the tip section 200 including electronic circuit board assembly 400 and fluid channeling component 600 and to provide protection to the internal components in the inner parts.

Tip cover 300 may include a front panel 320 having a transparent surface, window, or opening for front optical lens assembly 256, of front looking camera or viewing element 116. Front optical lens assembly 256 may include a plurality of lenses, static or movable, which may provide a field of view of 90 degrees or more, 120 degrees or more or up to essentially 180 degrees. Front optical lens assembly 256 may provide a focal length in the range of about 3 to 100 millimeters.

An optical axis of front looking camera or viewing element 116 may be essentially directed along the long dimension of the endoscope. However, since front viewing element 116 is typically a wide angle viewing element, its field of view may include viewing directions at large angles to its optical axis. Additionally, front panel 320 may include optical windows 242a, 242b and 242c of illuminators 240a, 240b and 240c, respectively. It should be noted that number of illumination sources used for illumination of the field of view may vary.

In addition, front panel 320 may include a working channel opening 340 of a working channel 640. In alternate embodiments, the front panel may include more than one working channel opening.

Jet channel opening 344 of jet channel 644 may also be located on front panel 320 of tip cover 300. Jet channel 644 may be configured for providing high-pressure jet of fluid such as water or saline for cleaning the walls of the body cavity.

Also located on front panel 320 of tip cover 300 is injector opening 346 of injector channel 646 having a nozzle 348 aimed at front optical lens assembly 256. Injector channel 646 may be configured for injecting fluid (liquid and/or gas) to wash contaminants such as blood, feces and other debris from a surface of front optical lens assembly 256 of front viewing element 116. Optionally, injector channel 646 may be configured for cleaning front optical lens assembly 256 and one, two, or all of optical windows 242a, 242b and 242c. Injector channel 646 may be fed by fluid such as water and/or gas which may be used for cleaning and/or inflating a body cavity.

Visible on the sidewall 362 of tip cover 300 is side optical lens assembly 256b for side viewing element 116b, which may be similar to front optical lens assembly 256 and optical windows 252a and 252b of illuminators 250a and 250b for side viewing element 116b. Also on the sidewall 362 of tip cover 300, on the opposing side of first side optical lens assembly 256b, is a second optical lens assembly for a second side viewing element, which may be similar to side optical lens assembly 256b and optical windows 252a and 252b of illuminators 250a and 250b for side viewing element 116b. The first side optical lens assembly 256b may provide a focal length in the range of about 3 to 100 millimeters.

An optical axis of the first side viewing element 116b may be essentially directed perpendicular to the long dimension of the endoscope. An optical axis of the second side viewing element may be essentially directed perpendicular to the long dimension of the endoscope. However, since each side viewing element typically comprises a wide angle camera, its field of view may include viewing directions at large angles to its optical axis. In accordance with some embodiments, each side viewing element has a field of view of 90 degrees or more, 120 degrees or more or up to essentially 180 degrees.

In addition, side injector opening 266 of side injector channel 666 may be located at distal end of sidewall 362. A nozzle cover 267 may be configured to fit side injector opening 266.

Additionally, nozzle cover 267 may include a nozzle 268 which may be aimed at side optical lens assembly 256b and configured for injecting fluid to wash contaminants such as blood, feces and other debris from a surface of side optical lens assembly 256b of side viewing element 116b. The fluid may include gas which may be used for inflating a body cavity. Optionally, nozzle 268 may be configured for cleaning both side optical lens assembly 256b and optical windows 252a and/or 252b.

According to some embodiments, side injector channel 666 may be configured to supply fluids for cleaning any of the tip elements (such as any optical assembly, optical lens assembly, windows, illuminators, and other elements).

Optionally, injector channel 646 and side injector channel 666 may be fed from same channel.

It is noted that according to some embodiments, although tip section 200 is presented herein showing one side thereof, the opposing side may include elements similar to the side elements described herein (for example, side viewing element, side optical lens assembly, injector(s), nozzle(s), illuminator(s), window(s), opening(s) and other elements).

Sidewall 362 may have a form of an essentially flat surface which assists in directing the cleaning fluid injected from injector channel 666 towards side optical lens assembly 256b and optical windows 252a and/or 252b. Lack of such flat surface may result in dripping of the cleaning fluid along the curved surface of tip section 200 of the endoscope without performing the desired cleaning action.

In accordance with an embodiment, the sidewall 362 is located in a notch/depression in the tip cover 300. This way, side injector opening 266 and corresponding side nozzle 268 may be elevated from the depressed sidewall 362 but still not significantly protrude from the level of cylindrical surface of the tip cover 300. According to an aspect of one embodiment, as shown in FIG. 59C, the sidewall 362 is located in a sufficiently well-defined or deep notch/depression 5963 in the tip cover 300 such that the lens assembly of side optical lens assembly 256b stays sufficiently embedded in the notch/depression 363 and well below the level 5900 of the cylindrical surface of the tip cover 300. The notch/depression 5963 protects the sidewall 362 and components thereof (side optical lens assembly 256b, side illuminators 250a, 250b and side nozzle 268) from both longitudinal and latitudinal mechanical shocks.

It is noted that according to some embodiments, tip section 200 may include more than one side looking camera. In this case, the side looking cameras may be installed such that their fields of view are substantially opposing. However, different configurations and number of side looking cameras are possible within the general scope of the current specification.

Fluid channeling component 600 includes a side service channel 650 having a side service channel opening 350.

Reference is now made to FIG. 1, along with FIGS. 3A, 3B, 3C, and 3D which show a perspective view of a tip section 200 of a multi jet endoscope assembly 6501 comprising a plurality of side jets, in addition to a front jet, to enable improved flushing according to an embodiment of the present specification.

Figure 3A:
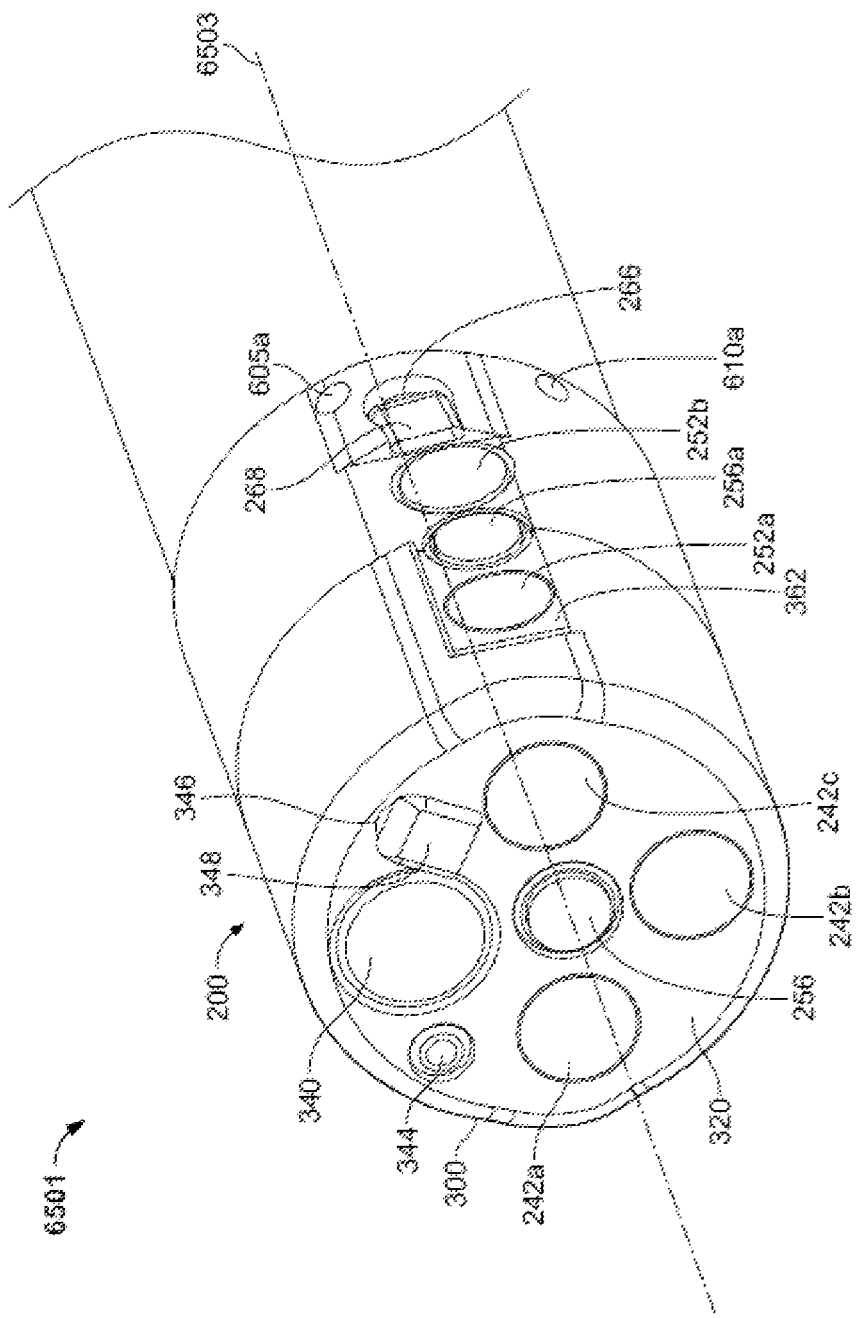
FIG. 3A illustrates a perspective view of a tip section of a multi jet endoscope assembly according to one embodiment of the present specification.
Figure 3D:
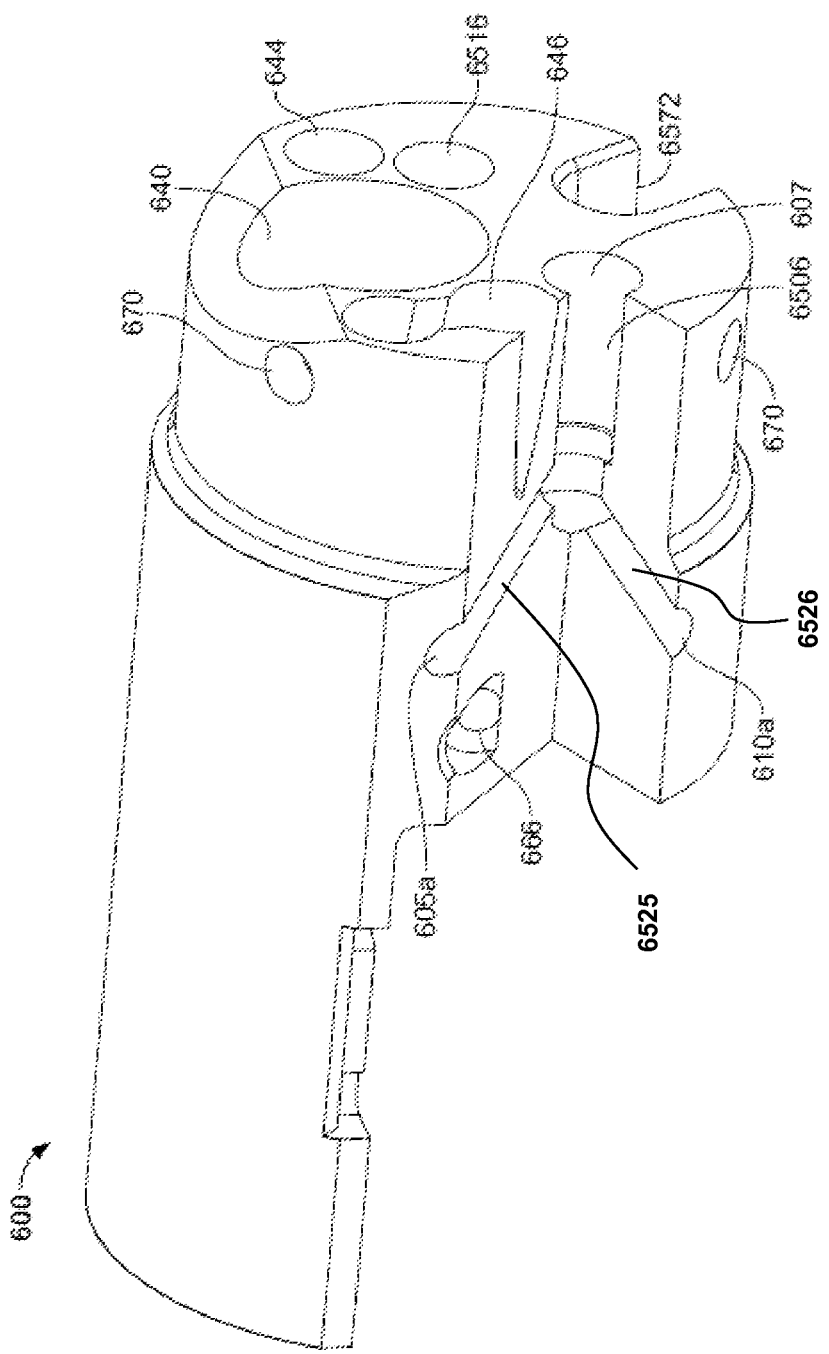
FIG. 3D illustrates a perspective view of a fluid channeling component of the multi jet endoscope assembly of FIG. 3A.

Tip cover 300 fits over the inner parts of the tip section 200 including electronic circuit board assembly 400 (shown in FIG. 1) and fluid channeling component 600 (shown in FIG. 3D) and to provide protection to the internal components in the inner parts. Holes 670 for pins for tip cover 300 are provided on fluid channeling component 600, as shown in FIG. 3D. Further, FIG. 3D shos a groove 6572 for an electrical cable. Tip cover 300 includes a front panel 320 having a transparent surface, window, or opening for front optical lens assembly 256, of front looking camera or viewing element 116, along with optical windows 242a, 242b and 242c of illuminators 240a, 240b and 240c, respectively.

The front panel 320 includes a working channel opening 340 of a working channel 640 and jet channel opening 344 of jet channel 644. Jet channel 644 is configured for providing a high-pressure jet of fluid, such as water or saline, for cleaning the walls of the body cavity. Also located on front panel 320 of tip cover 300 is injector opening 346 of injector channel 646 having a nozzle 348 aimed at front optical lens assembly 256. Injector channel 646 is configured for injecting fluid (liquid and/or gas) to wash contaminants such as blood, feces and other debris from a surface of front optical lens assembly 256 of front looking camera or viewing element 116. Optionally, injector channel 646 may be configured for cleaning at least a surface of front optical lens assembly 256 and one, two, or all of optical windows 242a, 242b and 242c. Injector channel 646 is fed by fluid such as water and/or gas which may be used for cleaning and/or inflating a body cavity. In one embodiment, the optical axis of the front looking camera or viewing element 116 is essentially directed along the central longitudinal axis 6503 that runs through the long dimension of the tip of the endoscope 6501.

FIG. 3B shows sidewall 362 of tip cover 300 comprising a transparent surface, window, or opening to side optical lens assembly 256a for a side looking viewing element, which may be similar to front optical lens assembly 256, and optical windows 252a and 252b of illuminators for the side looking viewing element. Also, as shown in FIG. 3C, the sidewall 362 of tip cover 300 on the opposing side to side optical lens assembly 256a is an optical lens assembly 256b for side looking viewing element 116b, and optical windows 252a and 252b of corresponding illuminators for side looking viewing element 116b. In one embodiment, the optical axis of one or both of the side looking viewing elements or cameras are essentially perpendicular to the optical axis (which is along the central longitudinal axis 6503 of the endoscope) of the front looking viewing element 116. In one embodiment, the optical axis of one or both of the side looking viewing elements forms an obtuse angle with the optical axis of the front viewing element 116 while in an alternate embodiment, the optical axis of one or both of the side viewing elements forms an acute angle with the optical axis of the front viewing element 116.

In addition, side injector openings 266 of corresponding side injector channels 666 are located at respective distal ends of the opposing sidewalls 362 as shown in FIGS. 3B and 3C. Nozzle covers 267 may be configured to fit the corresponding side injector openings 266. The nozzle covers include nozzles 268 that are aimed at side optical lens assemblies 256a, 256b and configured for injecting fluid to wash contaminants such as blood, feces and other debris from at least a surface of side optical lens assemblies 256a, 256b of the side looking viewing elements. The fluid may include gas which may be used for inflating a body cavity. Optionally, nozzles 268 may be configured for cleaning the side optical lens assembly and both optical windows on the opposing sides of the tip 200.

According to some embodiments, side injector channels 666 may be configured to supply fluids for cleaning any of the tip elements (such as any optical assembly, optical lens assembly, windows, illuminators, and other elements). Optionally, injector channel 646 and side injector channels 666 may be fed from the same channel.

As shown in FIGS. 3A through 3D, in accordance with an embodiment, two side jet openings 605a, 610a, fed by a common side jet channel 6506, are provided around the side periphery at the proximal end of the tip 200. Thus, the two side jet openings 605a, 610a which are fed by common side jet channel 6506 form a Y-shaped fluid conduit, described in greater detail below. The manifold shown in FIG. 3D includes a housing having a partially cylindrical shape with a curved top surface, a partially curved first side and a partially curved second side, wherein manifold housing is formed from a base portion with a first width, a first length, and a proximal surface and an elongated portion, which is attached to the base portion, with a second width, a second length, and a distal surface, wherein the first width is greater than the second width and the first length is less than the second length. A first channel 640 extends from the base portion through the elongated portion, wherein the first channel 640 has an entrance port positioned on said proximal surface of the base portion and an exit port positioned on a distal surface of the elongated portion. A second channel 644 extends from the base portion through the elongated portion, wherein the second channel 644 has an entrance port positioned on said proximal surface of the base portion and an exit port positioned on a distal surface of the elongated portion.

The Y-shaped fluid conduit comprises a central stem portion or common side jet channel 6506, a first prong portion 6525, and a second prong portion 6526, wherein the central stem portion 6506 extends from an entrance port 607 on the proximal surface of the base portion through the base portion, wherein the first prong portion 6525 extends from an end of the central portion through the base portion to an exit port on the partially curved first side; and wherein the second prong portion 6526 extends from an end of the central portion through the base portion to an exit port on the partially curved second side. In one embodiment, the exit port extending from the first prong portion 6525 forms side jet opening 605a while the exit port extending from the second prong portion 6526 forms side jet opening 610a.

A third channel 646 extends from an entrance port on the proximal surface of the base portion through to an exit port on the partially curved first side. A fourth channel 6516 extends from an entrance port on the proximal surface of the base portion through to an exit port on the partially curved second side. Each of the first, second, third, and fourth channels are fluidically isolated and separated from each other.

The common side jet channel 6506 has an entry port 607 at a proximal end of the fluid channeling component 600. Similarly, two side jet openings 605b, 610b, fed by another common side jet channel, are provided on the opposite side of side jet openings 605*a* and 610*a*. In one embodiment the two side jet openings 605*a*, 605*b*, 610*a*, 610*b* on either side of the tip are positioned in such a way that the side injector openings 266 (one on both sides of the tip) are situated between them. Additionally, in one embodiment, the two side jet openings 605*a*, 605*b*, 610*a*, 610*b* on either side of the tip are positioned close to the side optical lens assemblies 256*a*, 256*b* of the side looking cameras (on both sides of the tip) such that when fluid is ejected from the side jet openings it is propelled at an approximately 45 degree angle and past the cameras, so that a physician can see the fluid being expelled. The fluid can be water or saline.

It should be noted that, in alternate embodiments, side jet openings can be configured around the side periphery in any suitable number, including 2, 4, 6, or 8. Also, the side jet openings can have a plurality of angular configurations causing fluid to exit at different angles relative to a lateral plane that includes the side optical lens assemblies of side viewing elements and the optical windows of the corresponding illuminators but not the front optical lens assembly of the front viewing element. In one embodiment, the optical axis of the side viewing elements is perpendicular to the lateral plane as well as the optical axis of the front viewing element which is along the central longitudinal axis 6503 of the endoscope. These angles of fluid exit can range from 45 to 60 degrees or 120 to 135 degrees relative to the lateral plane. Acute angles of exit of 45 to 60 degrees enable fluid to be expelled in the direction of movement of the endoscope while obtuse angles of exit of 120 to 135 degrees enable fluid to be expelled in the direction opposite to the direction of movement of the endoscope, thereby aiding the endoscope movement within a body cavity. This is because, if the jet is directed in an opposite direction of movement of the endoscope, the resistance of the colon walls may push the scope forward like a jet engine.

In accordance with one embodiment, the side jet openings are positioned 8.5 to 9.5 millimeters from the side optical lens assemblies on the circumference of the endoscope such that the fluid exiting the openings form angles ranging from 50 degrees to 60 degrees relative to a lateral plane containing the side optical lens assemblies and corresponding side optical windows (but not containing front optical lens assembly of the front viewing element). Also, the side jet openings have a diameter of about 1.4 to 1.7 millimeters, in one embodiment.

Figure 4A:
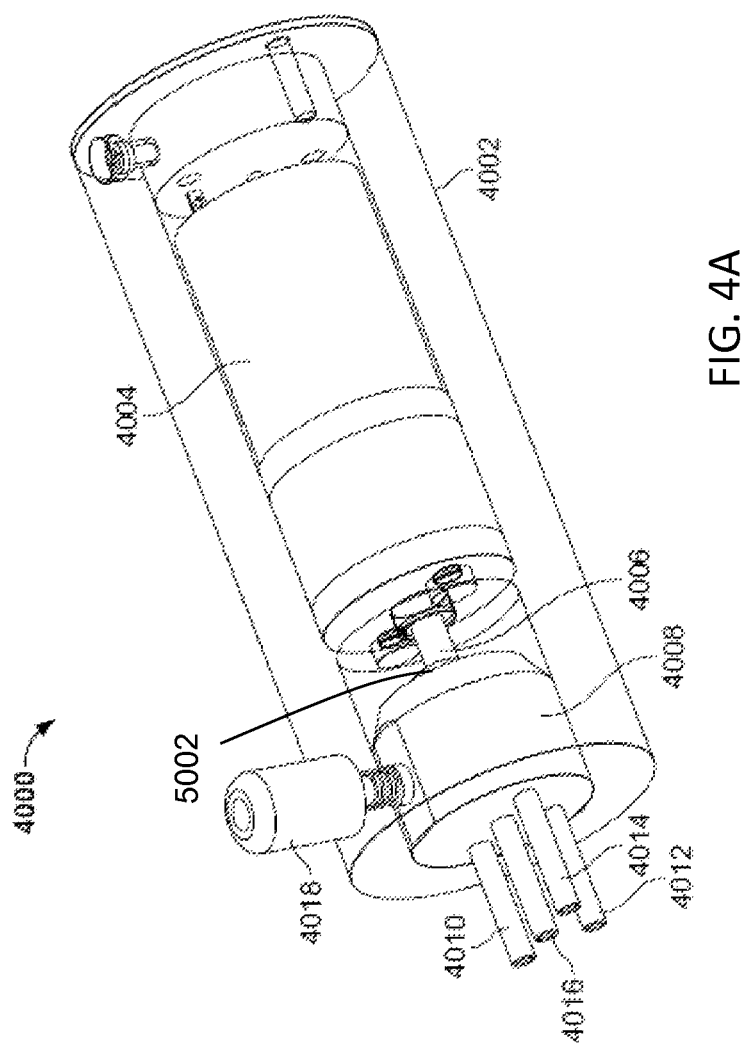
FIG. 4A illustrates a multi jet distributor pump, in accordance with an embodiment of the present specification.

Referring now to FIG. 1 and FIGS. 3A through 3D, in an embodiment, a jet distributor is provided to supply fluids to each of the side jet openings, such as 605*a*, 605*b*, 610*a*, 610*b* in the multi jet endoscope tip 6501 of FIGS. 3A through 3D, and the front jet 344. The jet distributor typically comprises three fluid channels to provide fluid to the front jet 344, right-side jets 605*a*, 610*a* and left-side-jets 605*b*, 610*b* in the endoscope tip 6501. FIG. 4A illustrates a multi jet distributor 4000, in accordance with an embodiment of the present specification. As illustrated, the multi jet distributor 4000 comprises a distributor motor housing 4002 and a distributor motor 4004 coupled with a motor shaft 4006 which in turn is coupled with a distributor rotating plug 5002 placed inside a distributor disc or cap 4008 adapted to channel fluid out into three exiting fluid pipelines 4010, 4012, and 4014, thereby supplying fluid to three jet openings (front jet 344, right-side-jets 605*a*, 610*a* and left-side-jets 605*b*, 610*b*) in the endoscope tip. The multi jet distributor 4000 further comprises an entering fluid pipeline 4016 that transports fluid from a fluid source, via a conventional jet pump, into the multi-jet distributor 4000. Locking element 4018 enables the distributor disc 4008 to be latched on to the motor shaft 4006. In various embodiments, different fluid distribution rates can be selected by varying the electric current applied to the distributor motor.

In one embodiment, jet distributor 4000 comprises two fluid channels to provide fluid to the front jet 344 and sides jets 605*a*, 605*b*, 610*a*, 610*b* in the endoscope tip. The multi jet distributor 4000 comprises a distributor motor housing 4002 and a distributor motor 4004 coupled with a motor shaft 4006 which, in turn, is coupled with a distributor disc 4008 adapted to channel fluid out into two exiting fluid pipelines, thereby supplying fluid to three jet openings in the endoscope tip. In this embodiment, the two sides jets are fed by a common jet channel split into two pipelines upon entering the endoscope tip; one provides fluids to the right-side-jets and the other to the left-side-jets.

Figure 4B:
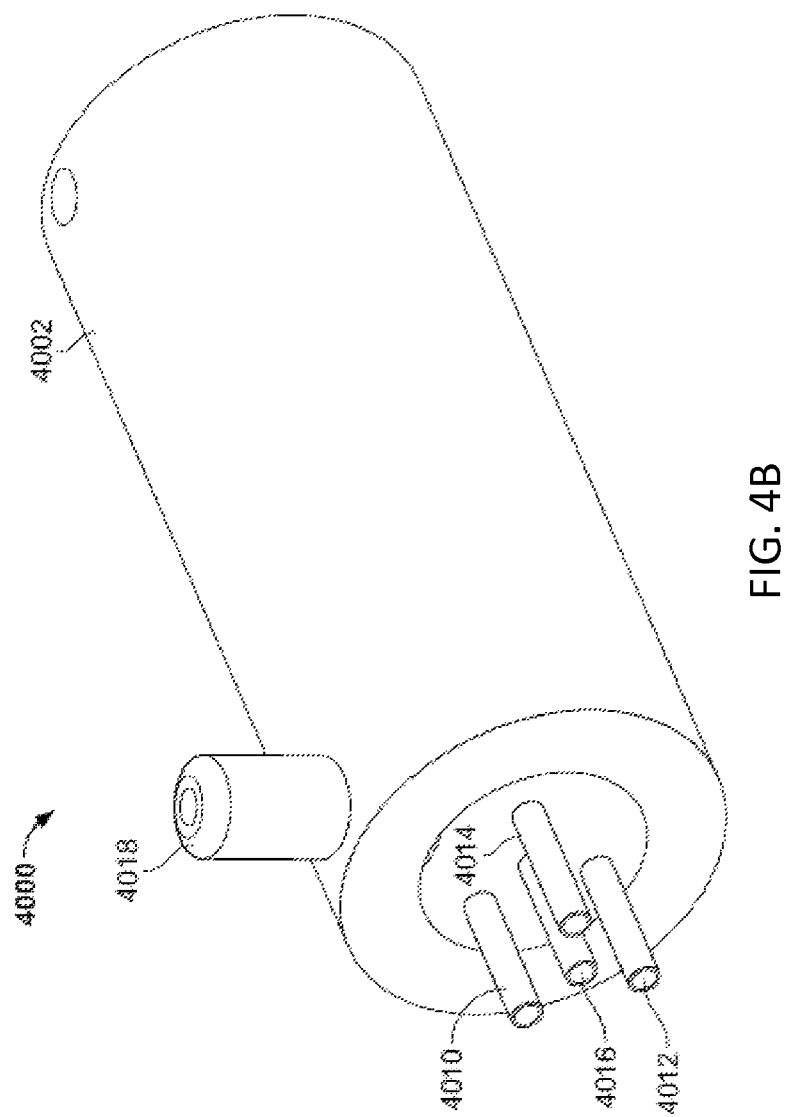
FIG. 4B illustrates another view of the multi jet distributor pump of FIG. 4A, in accordance with an embodiment of the present specification.
Figure 4C:
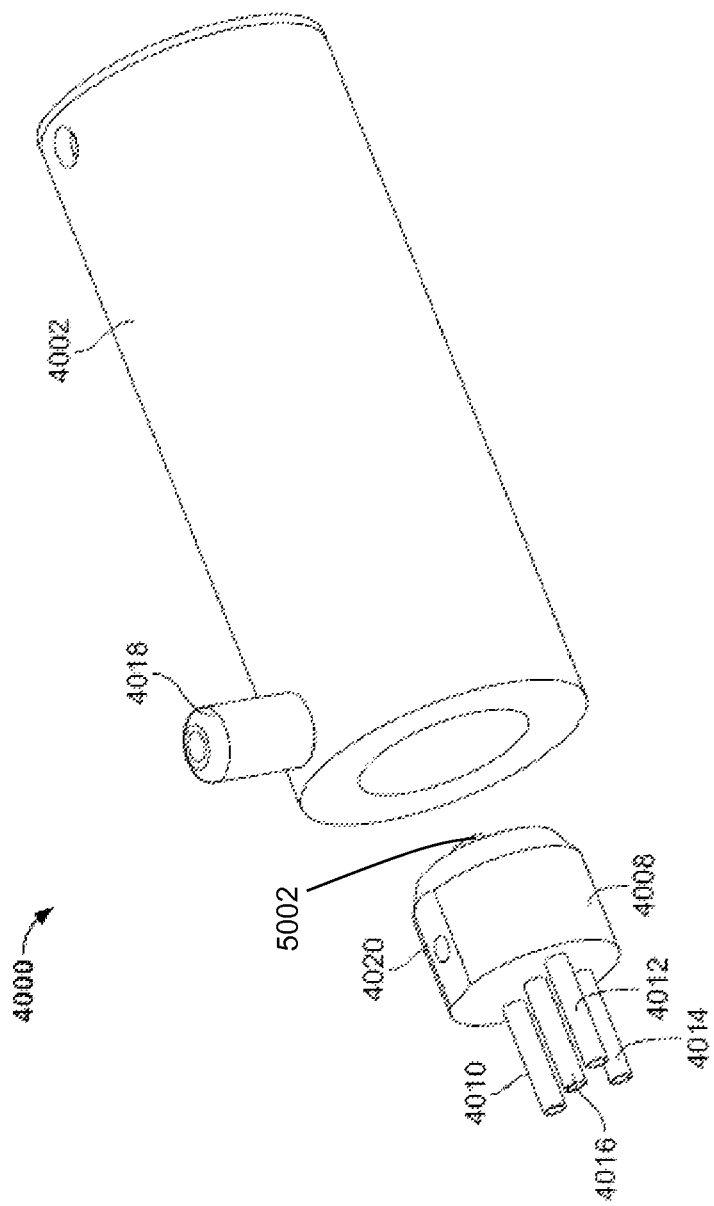
FIG. 4C illustrates yet another view of the multi jet distributor pump of FIG. 4A, in accordance with an embodiment of the present specification.

FIGS. 4B and 4C illustrate additional views of the multi jet distributor pump 4000, in accordance with embodiments of the present specification. As illustrated in FIG. 4C, the distributor disc 4008 is physically detachable from the distributor motor housing 4002 and can be latched in, and out, of the distributor motor housing 4002 by using the locking element 4018 which is fitted in a groove 4020 of the distributor disc 4008.

In one embodiment, the distributor disc 4008 is a substantially cylindrical structure comprising a plurality of circular slots for attaching with fluid pipelines. In an embodiment, the distributor disc 4008 comprises a slot for attaching with an entering fluid pipeline 4016 which has a diameter ranging from approximately 1 to 20 millimeters, and more specifically between 1 to 10 millimeters. In an embodiment, the distributor disc 4008 further comprises at least two slots for attaching with exiting fluid pipelines, each having a diameter ranging from approximately 1 to 20 millimeters, and more specifically between 1 to 10 millimeters. The circular slots on the face of the distributor disc 4008 attaching with the fluid pipelines are separated by a minimum distance. In an embodiment, the length of the entering and exiting pipelines is selected to minimize the overall space requirements of the distributor pump, yet achieve the fluid rate objectives of the present invention as described below. Also, in an embodiment, the fluid pipelines are connected to the distributor disc 4008 by using sealing members such as an O-ring or a gasket. During use, fluid pipelines are threaded and secured via threading onto the distributor disc 4008 and sealed thereto, using the sealing members. In an embodiment, the three exit pipelines connect to, or mate with, complementary fluid channels, which direct fluid through to the jet openings in the endoscope tip, via a main connector. In an embodiment, a universal luer connector is used to connect the fluid pipelines to the main connector. In other embodiments, any suitable connecting element may be used to connect the fluid pipelines to the main connector.

Three of the pipes which are positioned normal to the face of the distributor disc are exiting fluid pipelines 4010, 4012, and 4014 and operate to supply fluid to three jet openings in an endoscope tip. The fourth pipe which is positioned normal to the face of the distributor disc is an entering fluid pipeline 4016.

In various embodiments, a distributor rate within the multi jet distributor 4000 can vary from 30 revolutions per minute (rpm) to 100 rpm, and more specifically between 50-65 rpm. The distributor rate may also depend upon a fluid flow rate received into the multi jet distributor.

The distributor rate is defined as the revolutions per minute (rpm) of a distributor rotating plug contained within the distributor disc or cap and attached to the motor shaft, as described with reference to FIGS. 7A and 7B below.

In an embodiment, a first pipeline supplies fluid to a front panel of the endoscope, a second pipeline supplies fluid to one side of the tip, and a third pipeline supplies fluid to the other side of the tip. In another embodiment, only two pipelines enter the main connector, wherein a first pipeline supplies fluid to the front jet and a second supplies fluid to the side jets of the endoscope.

Figure 5A:
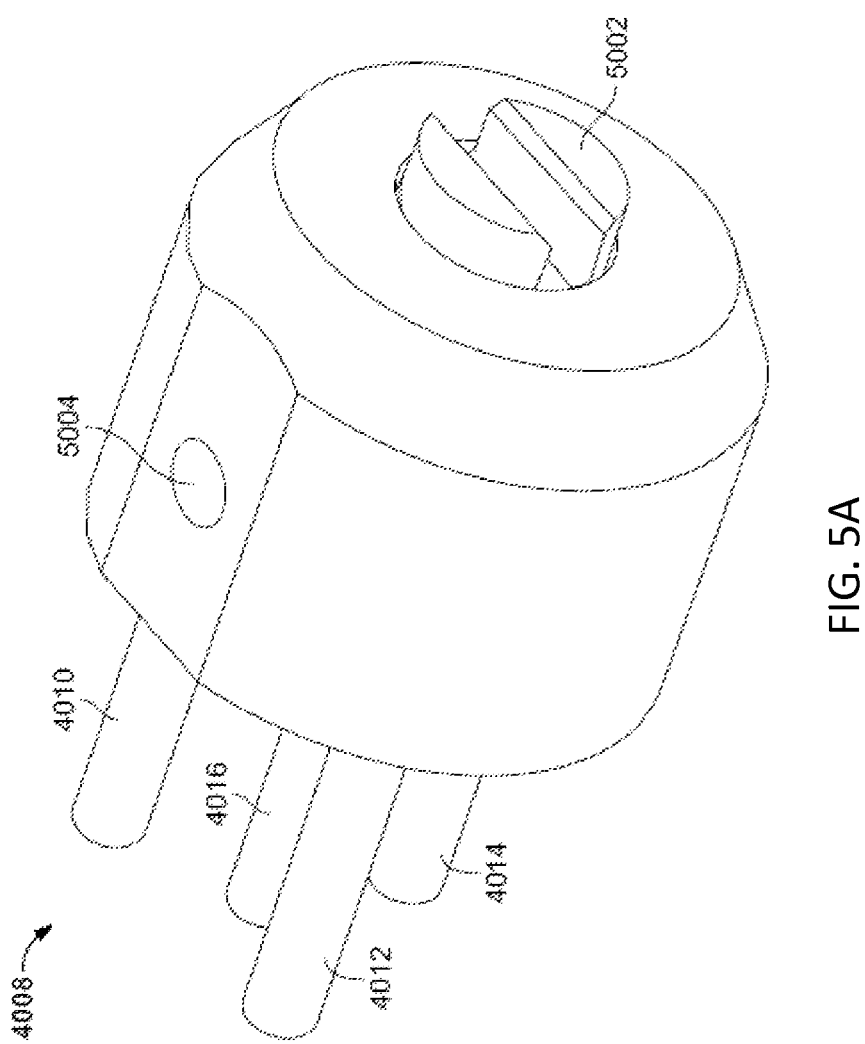
FIG. 5A illustrates a distributor disc of a multi jet distributor, in accordance with an embodiment of the present specification.
Figure 5B:
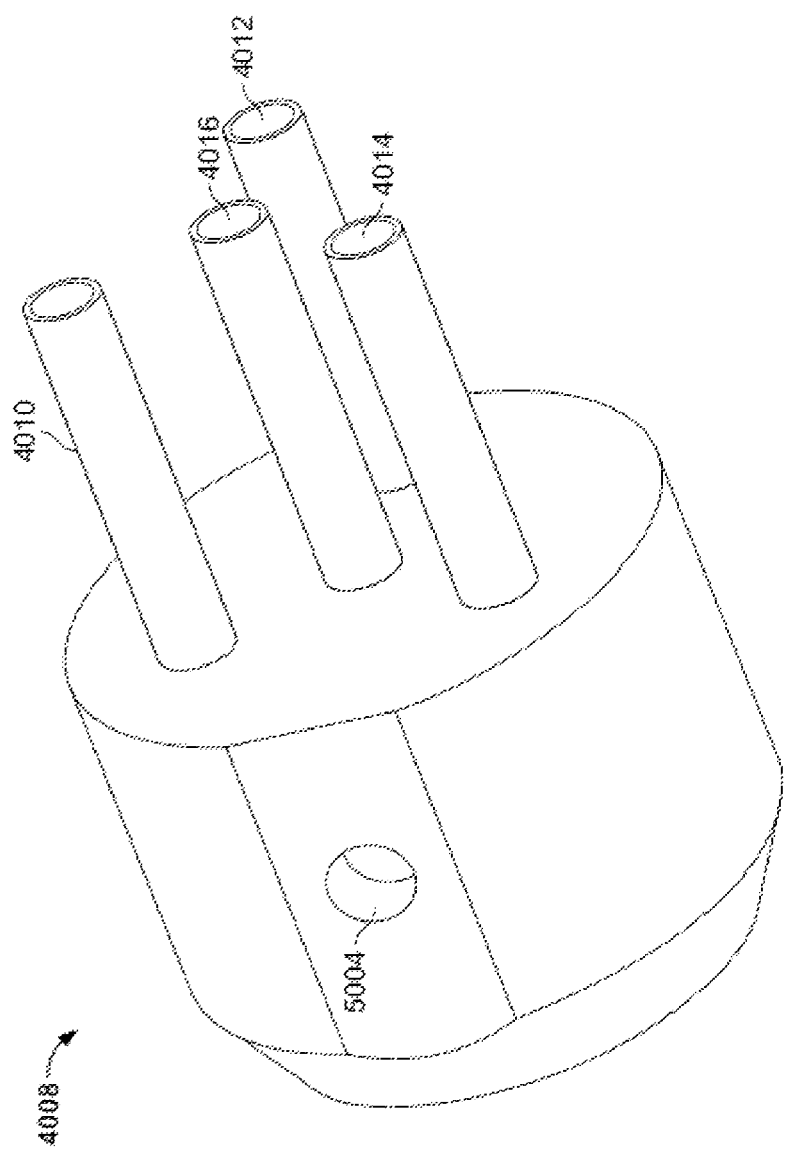
FIG. 5B illustrates another view of a distributor disc of a multi jet distributor, in accordance with an embodiment of the present specification.

FIG. 5A illustrates a distributor disc 4008 of a multi jet distributor, in accordance with an embodiment of the present specification. The disc 4008 comprises a distributor rotating plug 5002 for connecting the disc 4008 to the motor shaft 4006 (shown in FIG. 4A). A locking element 4018 (shown in FIGS. 4A-4C) may be fitted in a groove 5004 on the disc 4008 to connect the disc to the motor shaft 4006. FIG. 5B illustrates another view of the distributor disc 4008 of a multi jet distributor, in accordance with an embodiment of the present specification, showing the groove 5004, three exiting fluid pipelines 4010, 4012 and 4014 and one entering fluid pipeline 4016.

Figure 6A:
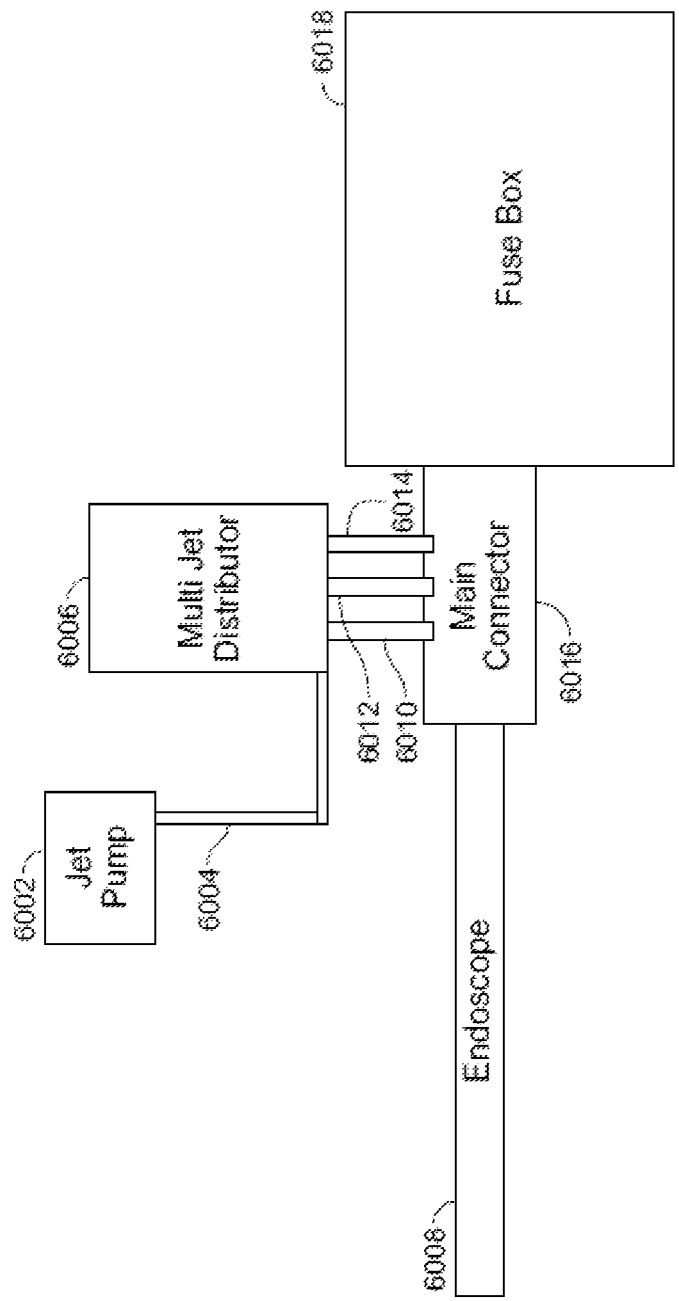
FIG. 6A is a block diagram illustrating the connection between a multi jet distributor and an endoscope, in accordance with an embodiment of the present specification.

FIG. 6A is a block diagram illustrating the connection between a multi jet distributor and an endoscope, in accordance with an embodiment of the present specification. A pump, such as jet pump 6002, pumps fluid from a fluid source, via an entering fluid pipeline 6004, into a multi-jet distributor 6006. The fluid is supplied by the multi-jet distributor 6006 to three jet openings in a tip of an endoscope 6008 via three exiting fluid pipelines 6010, 6012 and 6014 and a main connector 6016. In an embodiment, each of the three exiting fluid pipelines supplies fluid to a fluid channel of the endoscope 6008. In one embodiment, each exiting fluid pipeline is connected to main connector by a luer connector, or by any connecting system of small-scale fluid fittings used for making leak-free connections between a male-taper fitting and its mating female part on medical instruments. The main connector is also coupled with a controller unit 6018 that acts as a main control unit for the endoscope 6008.

In various embodiments, in order to activate the jet and wash a lumen in a patient's body, a doctor/physician operating the endoscope is required to push a button located either on a handle of the endoscope, on the main control unit, or on a control panel of the endoscope. Once the button is pressed, the multi jet distributor starts providing fluid at a pre-determined rate to each of the three fluid channels of the endoscope. In another embodiment, the doctor/physician may be required to push/step on a foot pedal to activate the jet-pump, which is in data communication with the foot pedal or other activation means. The jet-pump provides fluid to the multi jet distributor and at the same time activates the multi jet distributor motor. In various embodiments, the operating doctor/physician may change a rate of flow of fluid being supplied by the multi jet distributor dynamically during the operation.

In an embodiment, the multi jet distributor is located outside the endoscope system but is connected to a main control unit of the endoscope as illustrated in FIG. 6A. The multi jet distributor may connect to the main control unit by using a coupling system. In accordance with an embodiment of the present specification, the coupling system comprises a hanger plug and socket pair such that the hanger plug is integrally formed on a distributor disc or cap portion of the multi jet distributor while the hanger socket, to removably yet fixedly receive the hanger plug, is affixed to a side of the main control unit 6018.

In various embodiments, alternate connection systems that are easily connected/disconnected but securely fixed may be used. For example, the connection system may include a magnetic coupling pair where a first magnet is fixed to the multi-distributor jet and a second magnet, having polarity opposite to the first, is affixed to a side of the main control unit. Bringing the first magnet close to the second would result into a strong magnetic coupling to enable the multi jet distributor to be removably, yet securely, attached to the main control unit.

Additional examples may include clips, snaps, clasps, hooks, a female/male attachment pair, and other connection systems that enable removable, yet firm, coupling as would be advantageously evident to persons of ordinary skill in the art In another embodiment, the multi jet distributor is integrated into the control unit, such that the housing of the multi jet distributor is located inside the control unit.

Figure 6B:
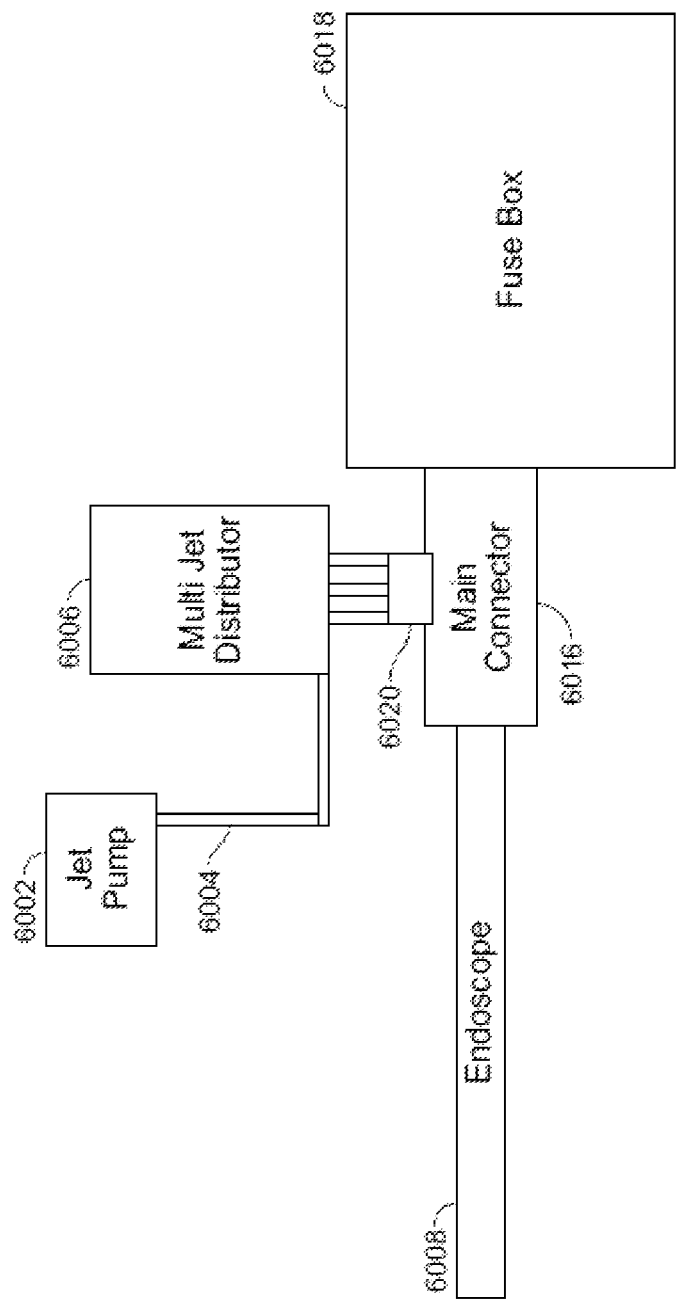
FIG. 6B is a block diagram illustrating another connection between a multi jet distributor and an endoscope, in accordance with an embodiment of the present specification.

FIG. 6B is a block diagram illustrating another connection between a multi jet distributor and an endoscope, in accordance with an embodiment of the present specification. As illustrated, the multi-jet distributor 6006 supplies fluid to three jet openings in a tip of an endoscope 6008 via a single exiting connector housing within the three pipelines exiting pipeline 6020. Hence, in the embodiment illustrated in FIG. 6B, a single fluid pipeline supplies fluid to the three fluid channels of the endoscope 6008.

FIG. 7A illustrates a sectional view of a distributor disc or cap of a multi jet distributor, in accordance with an embodiment of the present specification. A jet pump 7002 pumps a fluid via an entering (input) fluid pipeline or channel 7004 into a distributor disc or cap 7006, which in turn distributes the fluid into three streams being pumped out via three exiting (output) fluid pipelines or channels 7008, 7010 and 7012 (not shown in FIG. 7A) into a main connector 7014 by rotating a distributor rotating plug 5002, wherein the distributor rotating plug 5002 has a first end 5002a and a second end 5002b. The rotating plug 5002 is attached at a first end 5002a to the motor shaft (shown as 4006 in FIG. 4A). In one embodiment, as seen in FIG. 7A, a distributor element 7021 is attached to a second end 5002b of the rotating plug 5002 opposite said first end 5002a. The distributor element 7021, being physically attached to the rotating plug 5002, rotates within the distributor disc or cap 7006 as the motor is operated. The distributor element 7021 comprises a cylindrical body having a first end 7021a attached to said second end 5002b of said rotating plug 5002, and a second end 7021b opposite said first end. An L-shaped fluid pathway 7020 is positioned within the distributor element 7021 and includes an entrance opening 7022 at the second end 7021b of the distributor element 7021 and an exit opening 7023 in a side wall 7021c of the distributor element 7021.

Fluid is pumped from the jet pump 7002 into the entering fluid pipeline 7004. The entering fluid pipeline 7004 passes through the distributor disc or cap 7006 and is in fluid communication with the L-shaped fluid pathway 7020 of the distributor element 7021 via the entrance opening 7022. As the rotating plug 5002 and distributor element are rotated within the distributor disc or cap 7006 by the motor, the L-shaped fluid pathway 7020 of the distributor element 7021 is intermittently aligned with each of the exiting fluid pipelines 7008, 7010, and 7012 (seen in FIG. 7B). During rotation of the distributor element 7021, while one exiting fluid pathway is open, the remaining two are occluded. For example, as seen in FIG. 7A, the distributor element 7021 is positioned such that its L-shaped fluid pathway 7020 is aligned to, and in fluid communication with, exiting fluid pipeline 7008. Since the L-shaped fluid pathway 7020 is the only path for fluid to exit the distributor element 7021, exiting fluid pipelines 7010 and 7012 (seen in FIG. 7B) are effectively closed while exiting fluid pipeline 7008 is open. In another embodiment, the rotating plug is one solid piece without a distributor element, extending into the distributor disc or cap and containing an L-shaped fluid pathway.

FIG. 7B illustrates another sectional view of a distributor disc or cap of a multi jet distributor, in accordance with an embodiment of the present specification. The distributor disc or cap 7006 comprises an inlet for an entering fluid pipeline 7004 and three outlets for exiting fluid pipelines 7008, 7010 and 7012. It should be appreciated that the exiting fluid pipelines can number one, two, three, four or more.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A system for distributing fluid from a source external to an endoscope into a plurality of fluid channels positioned within the endoscope, comprising:
   a pump;
   a fluid distributor device having a fluid input channel coupled to said pump, a distributor rotating plug and a plurality of fluid output channels, wherein said distributor rotating plug includes an internal fluid pathway, said internal fluid pathway being in fluid communication with said fluid input channel and capable of being positioned, via rotational movement of said distributor rotating plug, into a plurality of configurations wherein, when in each of said plurality of configurations, said internal fluid pathway is in fluid communication with one of said plurality of said fluid output channels and is not in fluid communication with any one of the remaining said plurality of fluid output channels;
   a motor shaft coupled to said distributor rotating plug;
   a motor coupled to said motor shaft, wherein, upon activating the motor, the motor causes the distributor rotating plug to rotate, thereby intermittently aligning said internal fluid pathway with each of said plurality of fluid output channels, allowing fluid to move from said fluid input channel, through the internal fluid pathway and successively into each of said plurality of fluid output channels; and
   at least one endoscope connector comprising said plurality of endoscope fluid channels, wherein said plurality of endoscope fluid channels are in fluid communication with the plurality of fluid output channels.

2. The system of claim 1, further comprising a distributing element attached to said distributor rotating plug and rotatably movable within said fluid distributor device, wherein said distributing element comprises said internal fluid pathway.

3. The system of claim 1, further comprising a housing, wherein said housing comprises said fluid distributor device, said motor and said motor shaft.

4. The system of claim 3, wherein the housing further comprises a locking element for fixedly positioning the fluid distributor device within the housing.

5. The system of claim 4, wherein the fluid distributor device further comprises a groove on an outer surface of said fluid distributor device for receiving the locking element.

6. The system of claim 1, wherein the fluid distributor device is substantially cylindrical.

7. The system of claim 1, wherein the fluid distributor device comprises a housing having an external surface and wherein each of the plurality of fluid output channels extends outward from said external surface.

8. The system of claim 1, wherein the fluid distributor device comprises at least three fluid output channels and wherein each of said at least three fluid output channels is separately and individually connected to at least three endoscope fluid channels.

9. The system of claim 1, wherein said at least one endoscope connector is positioned within said endoscope.

10. The system of claim 1, wherein said at least one endoscope connector is positioned within a main control unit external to said endoscope.

11. The system of claim 10, wherein said at least one endoscope connector comprises a plurality of connectors for connecting said plurality of endoscope fluid channels with said plurality of fluid output channels.

12. The system of claim 10, wherein said at least one endoscope connector comprises a single connector for connecting said plurality of endoscope fluid channels with said plurality of fluid output channels.

13. The system of claim 1, wherein said distributor rotating plug has a distributor rate ranging between 30 revolutions per minute (rpm) and 100 rpm.

* * * * *